United States Patent
Muller et al.

(10) Patent No.: US 6,521,238 B1
(45) Date of Patent: Feb. 18, 2003

(54) COMPOSITION CONTAINING AN OPACIFIER OR PEARLESCENT AGENT AND AT LEAST ONE FATTY ALCOHOL

(75) Inventors: Rainer Muller, Leopoldshafen (DE); Bernard Beauquey, Clichy (FR)

(73) Assignee: L'Oreal S.A. (FR)

( * ) Notice: Subject to any disclaimer, the term of this patent is extended or adjusted under 35 U.S.C. 154(b) by 0 days.

(21) Appl. No.: 09/361,604

(22) Filed: Jul. 26, 1999

(30) Foreign Application Priority Data

Jul. 27, 1998 (FR) .......................................... 98 09562

(51) Int. Cl.$^7$ ................................................ A61K 6/00
(52) U.S. Cl. .................. 424/401; 424/70.1; 424/70.11; 424/70.12; 424/70.13; 424/70.19; 424/70.21; 424/70.22; 424/70.25; 424/70.24; 424/70.27; 424/70.28; 424/70.31
(58) Field of Search ............................ 424/70.1, 70.11, 424/70.12, 70.13, 70.19, 70.21, 70.22, 70.23, 70.24, 70.27, 70.28, 70.31, 401

(56) References Cited

U.S. PATENT DOCUMENTS

| | | | |
|---|---|---|---|
| 4,544,498 A | * 10/1985 | Suzuki | |
| 5,015,471 A | * 5/1991 | Birtwistle et al. | |
| 5,275,755 A | * 1/1994 | Sebag et al. | 252/174 |
| 5,324,507 A | * 6/1994 | Dublief et al. | 424/70 |
| 5,529,721 A | 6/1996 | Salka et al. | 252/546 |
| 5,656,200 A | * 8/1997 | Boettcher et al. | 252/307 |
| 5,888,487 A | 3/1999 | Baumoeller et al. | 424/70.1 |
| 6,306,916 B1 | 10/2001 | Ansmann et al. | 516/77 |
| 6,309,628 B1 | 10/2001 | Ansmann et al. | 424/70.12 |
| 6,365,168 B1 | 4/2002 | Ansmann et al. | 425/401 |

FOREIGN PATENT DOCUMENTS

| | | |
|---|---|---|
| DE | 41 03 551 A1 | 8/1992 |
| DE | 41 27 230 | 2/1993 |
| DE | 195 11 569 A1 | 10/1996 |
| DE | 195 11 570 A1 | 10/1996 |
| DE | 195 11 571 A1 | 10/1996 |
| DE | 195 11 572 A1 | 10/1996 |
| DE | 196 22 968 | 12/1997 |
| DE | 196 46 867 | 12/1997 |
| DE | 196 46 869 C1 | 12/1997 |
| EP | 0 181 773 B1 | 5/1986 |
| EP | 0 407 042 A2 | 1/1991 |
| EP | 0 457 688 | 11/1991 |
| EP | 0 498 716 | 8/1992 |
| EP | 0 581 193 A2 | 2/1994 |
| JP | 63-295505 | 12/1988 |
| JP | 65-9916 | 1/1989 |
| WO | WO 92/10162 | 6/1992 |
| WO | WO 95/13863 | 5/1995 |
| WO | WO 96/21424 | 7/1996 |
| WO | WO 97/47274 | 12/1997 |
| WO | WO 97/47281 | 12/1997 |
| WO | WO 98/03155 | 1/1998 |
| WO | WO 98/20844 | 5/1998 |

OTHER PUBLICATIONS

English language Derwent Abstract of JP 60 038 310; Feb. 27, 1985.
English language Derwent Abstract of JP 63 284 113; Nov. 21, 1988.
English language Derwent Abstract of JP 02 004 709; Jan. 9, 1990.
English language Derwent Abstract of DE 41 27 230.
English language Derwent Abstract of DE 196 22 968.

* cited by examiner

*Primary Examiner*—Thurman K. Page
*Assistant Examiner*—Lakshmi Channavajjala
(74) *Attorney, Agent, or Firm*—Finnegan, Henderson, Farabow, Garrett & Dunner

(57) ABSTRACT

Compositions comprising at least one surfactant base, at least one linear, saturated, long-chain fatty alcohol containing at least 50% by weight, relative to the total weight of said at least one linear, saturated, long-chain fatty alcohol, of at least one linear, saturated, long-chain fatty alcohol containing 22 carbon atoms, and at least one additional ingredient chosen from opacifiers and pearlescent agents. The invention also relates to the use of such fatty alcohols or mixture of fatty alcohols to give a pearling effect to and/or to enhance the pearling effect of compositions comprising at least one surfactant base and at least one additional ingredient chosen from opacifiers and pearlescent agents. The compositions according to the invention are used in particular as rinse-out products, in particular for washing and conditioning keratin substances, such as human hair.

45 Claims, No Drawings

COMPOSITION CONTAINING AN OPACIFIER OR PEARLESCENT AGENT AND AT LEAST ONE FATTY ALCOHOL

The present invention relates to a composition comprising:
- at least one surfactant base,
- at least one linear, saturated, long-chain fatty alcohol, including, of course, a mixture of fatty alcohols, comprising at least 50% by weight relative to the total weight of the at least one linear, saturated, long-chain fatty alcohol, of at least one linear, saturated, long-chain fatty alcohol containing 22 carbon atoms, and
- at least one additional ingredient chosen from opacifiers and pearlescent agents; to the use of this composition as a pearlescent base, i.e. a pearling agent; and to a cosmetic composition comprising, in a cosmetically acceptable medium,
- at least one surfactant base,
- at least one linear, saturated, long-chain fatty alcohol comprising at least 50% by weight, relative to the total weight of the at least one linear, saturated, long-chain fatty alcohol, of at least one linear, saturated, long-chain fatty alcohol containing 22 carbon atoms, and
- at least one additional ingredient chosen from opacifiers and pearlescent agents, and
- at least one conditioner for keratin substances.

The invention also relates to the use of the composition as an agent for suspending insoluble conditioners, such as conditioners that are insoluble in water.

It is well known that hair which has been sensitized (i.e. damaged and/or embrittled) to varying degrees under the action of atmospheric agents or under the action of mechanical or chemical treatments, such as dyeing, bleaching and/or permanent-waving operations, is often difficult to disentangle and to style, and lacks softness.

It has already been recommended to use conditioners, in particular insoluble conditioners, in compositions for washing or caring for keratin substances such as the hair in order to facilitate disentangling of the hair and to make it soft, shiny and supple.

Given the insoluble nature of certain conditioners such as, for example, silicones or oils, it is sought to keep the conditioners uniformly dispersed in the medium without, however, reducing the viscosity or the detergent or lathering properties of the compositions. The silicones should also be delivered onto the keratin substances to be treated so as to give them, after the application, properties of softness, sheen and disentanglement.

It is also known that products, in particular cosmetic products, which have an iridescent, shimmering or metallized appearance or effect are widely favored by consumers on account of their aesthetic appeal and the fact that they give the product an appearance of richness. The agents which provide this effect are pearling agents generally comprising crystals which remain dispersed in the compositions and which reflect light.

The term "pearling agent" means an agent which produces an iridescent, shimmering or metallized appearance or effect. In the present application, "pearlescent base" refers to a composition which can act as a pearling agent. Compositions according to the present invention can be used as a pearlescent base. A "pearlescent agent" is a compound or substance which can act as a pearling agent.

Few means are currently available for effectively keeping insoluble conditioners in suspension, since this is a difficult problem to solve; to this end, it has already been proposed to use long-chain ester derivatives or polysaccharides such as xanthan gum. However, long-chain ester derivatives can present crystallization problems which lead to a change in the viscosity of the compositions over time; gelling agents also have drawbacks, namely, on the one hand, it is difficult to develop a foam with detergent compositions containing xanthan gum (poor foam initiation), and, on the other hand, the compositions lack a smooth texture and they flow in blobs, which users do not appreciate.

Long-chain ether or thioether derivatives, such as those described in European patent application EP 457,688 and PCT application WO 98/03155, are also known. However, these agents opacify the compositions while giving them no or insufficient pearling effect.

It has already been attempted to improve the pearling effect by adding thickeners and/or other pearlescent agents, but, in this case, the viscosity becomes too large and/or the composition is no longer stable.

The inventors have discovered, and it is this which forms the subject of the invention, that the use of at least one linear, saturated, long-chain fatty alcohol, including of course, a mixture of such fatty alcohols, comprising at least 50% by weight relative to the total weight of the at least one linear, saturated, long-chain fatty alcohol, of at least one linear, saturated, long-chain fatty alcohol containing 22 carbon atoms gives a pearling effect to and/or improves the pearling effect of compositions comprising at least one surfactant base and at least one additional ingredient chosen from opacifiers and pearlescent agents.

One subject of the invention is thus compositions comprising at least one surfactant base, at least one linear, saturated, long-chain fatty alcohol comprising at least 50% by weight relative to the total weight of the at least one linear, saturated, long-chain fatty alcohol, of at least one linear, saturated, long-chain fatty alcohol containing 22 carbon atoms, and at least one additional ingredient chosen from opacifiers and pearlescent agents.

The compositions according to the invention can be used as a pearlescent base for cosmetic compositions, to give a pearling effect which is better than that obtained with only the opacifier and/or pearlescent agent.

Another subject of the invention is the use of at least one linear, saturated, long-chain fatty alcohol comprising at least 50% by weight relative to the total weight of the at least one linear, saturated, long-chain fatty alcohol, of at least one linear, saturated, long-chain fatty alcohol containing 22 carbon atoms, and of an opacifier, as a pearlescent base.

The compositions can show very good homogeneity and good stability of the pearling agent, as well as a viscosity which is satisfactory for applying them to keratin substances.

Other subjects of the invention will become apparent on reading the description and the examples which follow.

The at least one linear, saturated, long-chain fatty alcohol or mixtures of such fatty alcohols comprising at least 50% by weight relative to the total weight of the at least one linear, saturated, long-chain fatty alcohol, of at least one linear, saturated, long-chain fatty alcohol containing 22 carbon atoms, more particularly comprises at least 70% by weight, relative to the total weight of the at least one linear, saturated, long-chain fatty alcohol, of at least one linear, saturated, long-chain fatty $C_{22}$ alcohol.

Generally, as in the case of the use of the commercial product, Nafol 1822 C from Condea, mentioned below, the at least one linear, saturated, long-chain fatty alcohol is present as a mixture of alcohols. The mixture can, for example, contain $C_{16}$ to $C_{24}$ fatty alcohols. Nafol 1822 C is referenced as behenyl alcohol in the Seventh Edition of the International Cosmetic Ingredient Dictionary, Volume 1, page 123 and is defined to be a mixture of fatty alcohols containing chiefly n-docosanol, a $C_{22}$ alcohol. In the mixtures of alcohols of the present invention, $C_{16}$ and $C_{24}$ fatty alcohols each generally represent less than 2% by weight, and the $C_{18}$ chains less than 10% by weight, relative to the total weight of the alcohol mixture. Of course, as defined above, with respect to the mixtures of alcohols, the $C_{22}$ alcohol is at least 50% of the mixture of alcohols.

Such fatty alcohols are, in particular, the products sold, as mentioned above, under the name Nafol 1822 C by the company Condea. Nafol 1822 C contains about 0.5% of $C_{16}$, 4–6% of $C_{18}$, 15–19% of $C_{20}$, 74–78% of $C_{22}$ and about 1.5% of $C_{24}$. Another representative mixture of fatty alcohols is the product sold under the name Nafol 2298 by the company Condea, which contains 98% $C_{22}$ alcohol.

The pearlescent agents and/or opacifiers which can be used according to the invention can preferably be chosen from:

i) fatty dialkyl ethers which are solid at a temperature of less than or equal to about 30° C., such as, for example, the dialkyl ethers of formula (I):

$$R\text{—}O\text{—}R' \qquad (I)$$

in which:

R and R', which may be identical or different, are chosen from saturated and unsaturated, linear and branched alkyl radicals containing from 12 to 30 carbon atoms and preferably from 14 to 24 carbon atoms, R and R' being chosen such that the compound of formula (I) is solid at a temperature of less than or equal to about 30° C. More particularly, R and R' are identical.

Preferably, R and R' are stearyl radicals.

The dialkyl ethers which can be used according to the invention in the compositions are insoluble in water. These compounds can be prepared according to the process described in German patent application DE 4,127,230, the disclosure of which is specifically incorporated by reference herein.

A distearyl ether which can be used in the context of the present invention is sold in particular under the name Cutina KE 3178 by the company Henkel.

ii) alcohols containing from 27 to 48 carbon atoms and comprising one or two ether, one or two thioether, one ether and one thioether, one sulphoxide and one ether, or one or two sulphoxide groups, wherein said alcohols have a structure corresponding to formula (II):

$$R1\text{—}X\text{—}[C_2H_3(OH)]\text{—}CH_2\text{—}Y\text{—}R2 \qquad (II)$$

in which R1 and R2, independently of each other, are chosen from linear $C_{12}$ to $C_{24}$ alkyl groups;

X is chosen from an oxygen atom, a sulphur atom, a sulphoxide group, and a methylene group;

Y is chosen from an oxygen atom, a sulphur atom, a sulphoxide group, and a methylene group;

when Y denotes a methylene group, the sum of the number of carbon atoms present in the groups R1 and R2 has a value ranging from 24 to 44 and preferably from 28 to 40 inclusive;

when Y does not denote a methylene group, the sum of the carbon atoms present in the groups R1 and R2 has a value ranging from 24 to 44 and preferably from 28 to 40 inclusive;

when X denotes sulphoxide, Y does not denote sulphur, and when Y denotes sulphoxide, X does not denote sulphur.

The compounds of formula (II) preferably used in accordance with the invention are those for which X denotes oxygen, Y denotes methylene and R1 and R2 denote radicals containing from 12 to 22 carbon atoms.

These compounds can be prepared according to European patent EP 457,688, the disclosure of which is specifically incorporated by reference herein.

According to the invention, the at least one linear, saturated long-chain fatty alcohol comprising at least 50% by weight of at least one linear, saturated, long-chain fatty alcohol containing 22 carbon atoms can represent from 0.5% to 15% by weight, preferably from 0.5% to 5% by weight and even more preferably from 0.5% to 3% by weight, relative to the total weight of the final composition.

According to the invention, the at least one additional ingredient chosen from opacifiers and pearlescent agents can represent from 0.5% to 15% by weight, preferably from 0.5% to 5% by weight and even more preferably from 1% to 3% by weight, relative to the total weight of the final composition.

The (at least one additional ingredient)/$C_{22}$ fatty alcohol ratio generally ranges from 0.2:1 to 8:1 and preferably from 0.3:1 to 5:1.

According to one preferred variant of the invention, the cosmetic compositions can also contain conditioners for keratin substances.

Another subject of the invention is thus novel cosmetic compositions, in particular foaming, conditioning, and washing compositions, comprising, in a medium which is cosmetically acceptable, at least one surfactant base, at least one conditioner, at least one linear, saturated, long-chain fatty alcohol or mixture of fatty alcohols comprising at least 50% by weight of at least one linear, saturated, long-chain fatty alcohol containing 22 carbon atoms, and at least one additional ingredient chosen from opacifiers and pearlescent agents.

The compositions thus prepared can also have good detergent and foaming properties and can make keratin substances, in particular the hair and/or the skin, feel very soft.

When they are applied to the hair, in addition to their possible washing properties, these compositions can also have hair conditioning properties, i.e. treated hair can be smooth, can disentangle easily and may feel soft. The hair can look natural and non-greasy.

The compositions according to the invention containing conditioners can be relatively stable. In particular, no uncontrolled release of the conditioner or thickener from the composition over time should take place. Lastly, the compositions can have a non-ropey and melting texture. The foam can be airy and rinse out easily.

Another subject of the invention involves the washing and conditioning process using such compositions.

Another subject of the invention is the use of at least one linear, saturated, long-chain fatty alcohol or mixture of fatty alcohols comprising at least 50% by weight, relative to the weight of the at least one linear, saturated, long-chain fatty alcohol, of at least one linear, saturated, long-chain fatty alcohol containing 22 carbon atoms, and at least one additional ingredient chosen from opacifiers and pearlescent agents, as an agent for suspending an insoluble conditioner in a cosmetic composition, in particular foaming, conditioning, and washing compositions, that contain at least one surfactant base in a cosmetically acceptable aqueous medium.

When the composition contains at least one conditioner, these conditioners can be chosen from poly-α-olefins, fluoro oils, fluoro waxes, fluoro gums, carboxylic acid esters, cationic polymers, silicones, mineral oils, plant oils, animal oils, ceramides, pseudoceramides, and mixtures thereof.

The cosmetically acceptable medium preferably consists of water or a mixture of water and at least one cosmetically or dermatologically acceptable solvent. Mention may be made, in particular, of cosmetically or dematologically acceptable solvents such as monoalcohols, polyalcohols, glycol ethers and fatty acid esters, which can be used alone or as a mixture.

Mention may be made more particularly of lower alcohols such as ethanol or isopropanol, polyalcohols such as diethylene glycol, glycerol or sorbitol, glycol ethers of glycol, glycol ethers of diethylene glycol, alkyl ethers of glycol, and alkyl ethers of diethylene glycol.

One possible composition according to the invention can also contain at least one additive chosen from sequestering agents, softeners, foam modifiers, dyes, other pearlescent agents, hydrating agents, antidandruff and antiseborrhoeic agents, other suspending agents, fatty acids containing linear or branched $C_{16}$–$C_{40}$ chains, hydroxy acids, electrolytes, thickeners, fatty acid esters, glyceryl esters of fatty acids, surfactants, fragrances, preservatives, sunscreens, proteins, vitamins, polymers and any other additive conventionally used in cosmetics.

These additives are present in the composition according to the invention in proportions which can range from 0 to 40% by weight relative to the total weight of the composition. The precise amount of each additive depends on its nature and can readily be determined by a person skilled in the art.

Needless to say, a person skilled in the art should take care to select the optional compound(s) to be added to the composition according to the invention such that the advantageous properties intrinsically associated with the composition in accordance with the invention are not, or are not substantially, adversely affected by the addition envisaged.

The compositions according to the invention can be in the form of a gel, a milk, a cream, a lotion, or a foam. One skilled in the art may thicken or dilute, for example, the resulting lotion as desired.

The compositions in accordance with the invention can be used for treating keratin substances, especially human keratin substances such as the hair, the skin, the eyelashes, the eyebrows, the nails, the lips or the scalp, and more particularly the hair.

The compositions can also be used for washing and cleansing keratin substances such as the hair and the skin.

The compositions according to the invention are generally used as products in particular for washing, caring for, conditioning or maintaining the hair style or for shaping keratin substances such as the hair.

The compositions of the invention can be, more particularly, in the form of a shampoo, a rinse-out or leave-in conditioner, compositions for permanent-waving, straightening, dyeing or bleaching the hair, or alternatively in the form of compositions to be applied before or after dyeing, bleaching, permanent-waving or straightening the hair, or between two steps of a permanent-waving or hair-straightening operation. Preferably, the compositions are washing and foaming compositions for the hair and/or the skin.

In particular, the compositions according to the invention are foaming detergent compositions such as shampoos, shower gels and bubble baths. In this embodiment of the invention, the compositions comprise a washing surfactant base, which is generally aqueous.

The surfactant(s) forming the washing or surfactant base can be chosen, impartially, alone or as mixtures, from anionic, amphoteric, nonionic, zwitterionic and cationic surfactants.

The minimum amount of surfactant base is that which is just sufficient to give the final composition a satisfactory foaming and/or detergent power.

Thus, according to the invention, the at least one surfactant base can preferably represent from 4% to 30% by weight, preferably from 6% to 25% by weight and even more preferably from 8% to 20% by weight, relative to the total weight of the final composition.

The surfactants which are suitable for forming the surfactant base according to the present invention can be, in particular, the following:

(i) Anionic Surfactant(s):

In the context of the present invention, their nature is not really a critical feature.

Thus, by way of example of anionic surfactants which can be used, alone or as mixtures, in the context of the present invention, mention may be made in particular (non-limiting list) of salts (in particular alkali metal salts, especially sodium salts, ammonium salts, amine salts, amino alcohol salts or magnesium salts) of the following compounds: alkyl sulphates, alkyl ether sulphates, alkyl amidoether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; alkyl sulphosuccinates, alkyl ether sulphosuccinates, alkylamide sulphosuccinates; alkyl sulphosuccinates; alkyl sulphoacetates; alkyl ether phosphates; acyl sarcosinates; acyl isethionates and N-acyl taurates, the alkyl or acyl radical of all of these different compounds preferably containing from 8 to 24 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; and acyl lactylates in which the acyl radical contains 8 to 20 carbon atoms. It is also possible to use weakly anionic surfactants, such as alkyl D-galactoside uronic acids and their salts, as well as polyoxyalkylenated ($C_6$–$C_{24}$)alkyl ether carboxylic acids, polyoxyalkylenated ($C_6$–$C_{24}$)alkylaryl ether carboxylic acids, polyoxyalkylenated ($C_6$–$C_{24}$)alkylamido ether carboxylic acids and their salts, in particular those containing from 2 to 50 ethylene oxide groups, and mixtures thereof.

Among the anionic surfactants preferably used according to the invention are alkyl sulphate and alkyl ether sulphate salts, and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116–178, the disclosure of which is expressly incorporated by reference herein), and, in the context of the present invention, their nature is not a critical feature. Thus, they can be chosen in particular from (non-limiting list) polyethoxylated, polypropoxylated or polyglycerolated fatty acids, alkylphenols, alpha-diols or alcohols having a fatty chain containing, for example, 8 to 18 carbon atoms, it being possible for the number of ethylene oxide or propylene oxide groups to range in particular from 2 to 50 and for the number of glycerol groups to range in particular from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as $(C_{10}-C_{14})$alkylamine oxides or N-acylaminopropylmorpholine oxides. It will be noted that the alkylpolyglycosides constitute nonionic surfactants that are particularly suitable in the context of the present invention.

(iii) Amphoteric or Zwitterionic Surfactant(s):

The amphoteric or zwitterionic surfactants, whose nature is not a critical feature in the context of the present invention, can be, in particular (non-limiting list), aliphatic secondary or tertiary amine derivatives in which the aliphatic radical is a linear or branched chain containing 8 to 18 carbon atoms and containing at least one water-solubilizing anionic group (for example carboxylate, sulphonate, sulphate, phosphate or phosphonate); mention may also be made of $(C_8-C_{20})$alkylbetaines, sulphobetaines, $(C_8-C_{20})$alkylamido$(C_1-C_6)$alkylbetaines or $(C_8-C_{20})$alkylamido$(C_1-C_6)$alkylsulphobetaines.

Among the amine derivatives, mention may be made of the products sold under the name Miranol, as described in U.S. Pat. Nos. 2,528,378 and 2,781,354, the disclosure of each of which is expressly incorporated by reference herein, and classified in the CTFA dictionary, 3rd edition, 1982, under the names Amphocarboxyglycinates and Amphocarboxypropionates. Amphocarboxyglycinates have the structure:

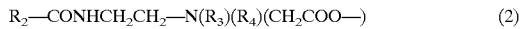

$$R_2\text{—CONHCH}_2\text{CH}_2\text{—N}(R_3)(R_4)(\text{CH}_2\text{COO—}) \qquad (2)$$

in which: $R_2$ is chosen from an alkyl radical derived from an acid $R_2$—COOH present in
hydrolysed coconut oil, a heptyl radical, a nonyl radical, and an undecyl radical,
$R_3$ denotes a beta-hydroxyethyl group, and
$R_4$ denotes a carboxymethyl group;
and Amphocarboxypropionates have the structure:

$$R_{2'}\text{—CONHCH}_2\text{CH}_2\text{—N(B)(C)} \qquad (3)$$

in which:
B represents —CH$_2$CH$_2$OX',
C represents —(CH$_2$)$_z$—Y', with z=1 or 2,
X' is chosen from a —CH$_2$CH$_2$—COOH group or a hydrogen atom,
Y' is chosen from a —COOH radical and a —CH$_2$—CHOH—SO$_3$H radical,
$R_{2'}$ is chosen from an alkyl radical of an acid $R_9$—COOH present in an oil chosen from coconut oil and hydrolysed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

By way of example, mention may be made of the cocoamphocarboxyglycinate sold under the trade name Miranol C2M concentrate by the company Rhodia Chimie.

(iv) Cationic Surfactants:

Among the cationic surfactants, whose nature, in the context of the present invention, is not a critical feature, mention may be made in particular (non-limiting list) of: salts of optionally polyoxyalkylenated primary, secondary or tertiary fatty amines; quaternary ammonium salts such as the chloride and bromide salts of tetraalkylammonium, alkylamidoalkyltrialkylammonium, trialkylbenzylammonium, trialkylhydroxyalkylammonium or alkylpyridinium radicals; imidazolines; or cationic amine oxides.

A subject of the invention is also a process for the cosmetic treatment of keratin substances such as the hair, which comprises applying a composition as defined above to the hair and then, after optionally leaving the composition to stand in the hair, in optionally rinsing it out with water.

The compositions according to the invention can be prepared mainly according to two procedures:

The first involves heating all the ingredients of the composition to about 80° C. with stirring and then allowing the mixture to cool to room temperature. The second involves preparing a pearlescent base which comprises the at least one surfactant base, the at least one additional ingredient chosen from opacifiers and pearlescent agents, the at least one linear, saturated long-chain fatty alcohol, water, a pH agent and optionally a preserving agent. The at least one additional ingredient and the at least one linear, saturated, long-chain fatty alcohol are added with stirring to the mixture of water and the at least one surfactant base preheated to about 80° C. The temperature is maintained for about 30 minutes and the mixture is then cooled to about 30° C. A required amount of pearlescent base so obtained is then added to a shampoo base at room temperature with the aid of a turbomixer.

The invention will now be illustrated more fully with the aid of the examples which follow, which cannot be considered as limiting it to the embodiments described. In the text hereinbelow, AM means Active Material.

EXAMPLE 1

Three shampoos, of the compositions below, were prepared: Compositions A and B are according to the invention and composition C is a comparative composition.

|  | A | B | C |
|---|---|---|---|
| Sodium lauryl ether sulphate oxyethylenated with 2.2 mol of ethylene oxide, as an aqueous solution containing 70% AM | 14.5 g AM | 14.5 g AM | 14.5 g Am |
| Cocoylbetaine as an aqueous solution containing 30% AM | 2.3 g AM | 2.3 g AM | 2.3 g AM |
| Dimethicone (Mirasil DM 500,000 from Rhodia Chimie) | — | 2 g | — |
| Hydroxyethylcellulose cross-linked with epichlorohydrin and quaternized with trimethylamine (JR 400 from Union Carbide) | — | 0.3 g AM | — |
| Mixture of cetyl alcohol and of 1-(hexadecyloxy)-2-octadecanol (opacifier) | 1.5 g | 1.5 g | 2.5 g |
| $C_{22}$ fatty alcohol (Nafol 1822 C from Condea) | 1 g | 1 g | — |
| Coconut acid monoethanolamide | 0.95 g | 0.95 g | 0.95 g |
| Preserving agents, fragrance | qs | qs | qs |
| Citric acid, 1 H$_2$O qs | pH 5.5 | pH 5.5 | pH 5.5 |
| Demineralized water qs | 100 g | 100 g | 100 g |

The pearling effect of compositions A and B according to the invention is better than that of composition C which contains only opacifier.

The foaming properties of compositions A and B are good.

Compositions A and B have good viscosity and are stable.

EXAMPLE 2

Three shampoos, of the compositions below, were prepared: Compositions A and B are according to the invention and composition C is a comparative composition.

|  | A | B | C |
|---|---|---|---|
| Sodium lauryl ether sulphate oxyethylenated with 2.2 mol of ethylene oxide, as an aqueous solution containing 70% AM | 14.5 g AM | 14.5 g AM | 14.5 g Am |
| Cocoylbetaine as an aqueous solution containing 30% AM | 2.3 g AM | 2.3 g AM | 2.3 g AM |
| Dimethicone (Mirasil DM 500,000 from Rhodia Chimie) | — | 2 g | — |
| Hydroxyethylcellulose quaternized with trimethylamine (JR 400 from Union Carbide) | — | 0.3 g AM | — |
| Distearyl ether (opacifier) | 1.5 g | 1.5 g | 2.5 g |
| $C_{22}$ fatty alcohol (Nafol 1822 C from Condea) | 1 g | 1 g | — |
| Coconut acid monoethanolamide | 0.95 g | 0.95 g | 0.95 g |
| Preserving agents, fragrance | qs | qs | qs |
| Citric acid, 1 H$_2$O qs | pH 5.5 | pH 5.5 | pH 5.5 |
| Demineralized water qs | 100 g | 100 g | 100 g |

The pearling effect of compositions A and B according to the invention is better than that of composition C which contains only opacifier.

The foaming properties of compositions A and B are good.

Compositions A and B have good viscosity and are stable.

When the Nafol 1822 C is replaced with a fatty alcohol comprising about 44% by weight of $C_{22}$ alcohol in composition A or B, it is seen that the pearling effect is entirely insufficient.

What is claimed is:

1. A cosmetic composition, which comprises:
   a) at least one surfactant base,
   b) at least one linear, saturated, long-chain fatty alcohol containing at least 50% by weight, relative to the total weight of said at least one linear, saturated, long-chain fatty alcohol, of at least one linear, saturated, long-chain fatty alcohol containing 22 carbon atoms, and
   c) at least one additional ingredient chosen from opacifiers and pearlescent agents, wherein said at least one additional ingredient is chosen from:
      i) fatty dialkyl ethers which are solid at a temperature of less than or equal to 30° C.,
      ii) alcohols containing from 27 to 48 carbon atoms and comprising one or two ether, one or two thioether, one ether and one thioether, one sulphoxide and one ether, or one or two sulphoxide groups, wherein said alcohols have a structure corresponding to formula (II):

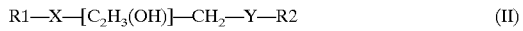

$$R1\!-\!X\!-\![C_2H_3(OH)]\!-\!CH_2\!-\!Y\!-\!R2 \quad (II)$$

in which R1 and R2, independently of each other, are chosen from linear $C_{12}$ to $C_{24}$ alkyl groups;

X is chosen from an oxygen atom, a sulphur atom, a sulphoxide group, and a methylene group;
   Y is chosen from an oxygen atom, a sulphur atom, a sulphoxide group, and a methylene group;
   wherein the sum of the number of carbon atoms present in the groups R1 and R2 has a value ranging from 24 to 44;
   wherein when X denotes sulphoxide, Y does not denote sulphur, and
   when Y denotes sulphoxide, X does not denote sulphur.

2. The composition according to claim 1, wherein said at least one linear, saturated, long-chain fatty alcohol contains at least 70% by weight, relative to the total weight of said at least one linear, saturated, long-chain fatty alcohol, of at least one linear, saturated, long-chain fatty alcohol containing 22 carbon atoms.

3. The composition according to claim 1, wherein said fatty dialkyl ethers are chosen from dialkyl ethers of formula (I):

$$R\!-\!O\!-\!R' \quad (I)$$

in which:
   R and R', which are identical or different, are chosen from saturated and unsaturated, linear and branched alkyl radicals containing from 12 to 30 carbon atoms, R and R' being chosen such that the compound of formula (I) is solid at a temperature of less than or equal to about 30° C.

4. The composition according to claim 3, wherein within said dialkyl ethers of formula (I), R and R' contain from 14 to 24 carbon atoms.

5. The composition according to claim 3, wherein within said dialkyl ethers of formula (I), R and R' are identical.

6. The composition according to claim 1, wherein within said alcohols which have a structure corresponding to formula (II), the sum of the number of carbon atoms present in the groups R1 and R2 has a value ranging from 28 to 40.

7. The composition according to claim 1, wherein said at least one additional ingredient is chosen from:
   i) distearyl ether, and
   ii) compounds of formula (II) for which X denotes oxygen, Y denotes methylene and R1 and R2 are chosen from radicals containing from 12 to 22 carbon atoms.

8. The composition according to claim 1, wherein said at least one linear, saturated, long-chain fatty alcohol is present in an amount ranging from 0.5% to 15% by weight relative to the total weight of the composition.

9. The composition according to claim 8, wherein said at least one linear, saturated, long-chain fatty alcohol is present in an amount ranging from 0.5% to 5% by weight relative to the total weight of the composition.

10. The composition according to claim 9, wherein said at least one linear, saturated, long-chain fatty alcohol is present in an amount ranging from 0.5% to 3% by weight relative to the total weight of the composition.

11. The composition according to claim 1, wherein said at least one additional ingredient is present in an amount ranging from 0.5% to 15% by weight relative to the total weight of the composition.

12. The composition according to claim 11, wherein said at least one additional ingredient is present in an amount ranging from 0.5% to 5% by weight relative to the total weight of the composition.

13. The composition according to claim 12, wherein said at least one additional ingredient is present in an amount ranging from 1% to 3% by weight relative to the total weight of the composition.

14. The composition according to claim 1, wherein said at least one surfactant base is present in an amount ranging from 4% to 30% by weight relative to the total weight of the composition.

15. The composition according to claim 14, wherein said at least one surfactant base is present in an amount ranging from 6% to 25% by weight relative to the total weight of the composition.

16. The composition according to claim 15, wherein said at least one surfactant base is present in an amount ranging from 8% to 20% by weight relative to the total weight of the composition.

17. The composition according to claim 1, further comprising at least one conditioner.

18. The composition according to claim 17, wherein said at least one conditioner is insoluble in water.

19. The composition according to claim 17, wherein said at least one conditioner is chosen from poly-α-olefins, fluoro oils, fluoro waxes, fluoro gums, carboxylic acid esters, polymers, silicones, mineral oils, plant oils, animal oils, ceramides, and pseudoceramides.

20. The composition according to claim 19, wherein said polymers are chosen from cationic polymers.

21. The composition according to claim 1, further comprising water or a mixture of water and at least one cosmetically or dermatologically acceptable solvent.

22. The composition according to claim 21, wherein said at least one cosmetically or dermatologically acceptable solvent is chosen from monoalcohols, polyalcohols, glycol ethers, and fatty acid esters.

23. The composition according to claim 22, wherein said at least one cosmetically or dermatologically acceptable solvent is chosen from ethanol, isopropanol, diethylene glycol, glycerol, sorbitol, glycol ethers of glycol, glycol ethers of diethylene glycol, alkyl ethers of glycol, and glycol ethers of diethylene glycol.

24. The composition according to claim 1, further comprising at least one additive.

25. The composition according to claim 24, wherein said at least one additive is chosen from sequestering agents, softeners, foam modifiers, dyes, hydrating agents, antidandruff agents, antiseborrhoeic agents, fatty acids containing linear or branched $C_{16}$–$C_{40}$ chains, hydroxy acids, electrolytes, thickeners, fatty acid esters, glyceryl esters of fatty acids, fragrances, preservatives, sunscreens, proteins, vitamins, and polymers.

26. The composition according to claim 24, wherein said at least one additive is present in an amount not more than 40% by weight relative to the total weight of the composition.

27. The composition according to claim 1, wherein said composition is in the form of a gel, a milk, a cream, a lotion, or a foam.

28. The composition according to claim 1, wherein said composition is a foaming detergent composition.

29. The composition according to claim 28, wherein said foaming detergent composition is chosen from shampoos, shower gels, and bubble baths.

30. A cosmetic composition, comprising
sodium lauryl ether sulphate oxyethylenated with 2.2 mol of ethylene oxide,
cocoylbetaine,
a linear, saturated, long-chain $C_{22}$ fatty alcohol,
cetyl alcohol, and
1-(hexadecyloxy)-2-octadecanol.

31. A cosmetic composition, comprising
sodium lauryl ether sulphate oxyethylenated with 2.2 mol of ethylene oxide,
cocoylbetaine,
dimethicone,
hydroxyethylcellulose crosslinked with epichlorohydrin and quaternized with trimethylamine,
a linear, saturated, long-chain $C_{22}$ fatty alcohol,
cetyl alcohol, and
1-(hexadecyloxy)-2-octadecanol.

32. A cosmetic composition, comprising
sodium lauryl ether sulphate oxyethylenated with 2.2 mol of ethylene oxide,
cocoylbetaine,
a linear, saturated, long-chain $C_{22}$ fatty alcohol, and
distearyl ether.

33. A cosmetic composition, comprising
sodium lauryl ether sulphate oxyethylenated with 2.2 mol of ethylene oxide,
cocoylbetaine,
dimethicone,
hydroxyethylcellulose crosslinked with epichlorohydrin and quaternized with trimethylamine,
a linear, saturated, long-chain $C_{22}$ fatty alcohol, and
distearyl ether.

34. A cosmetic composition, which comprises:
a) at least one surfactant base, chosen from:
   (i) Anionic surfactants, said anionic surfactants being chosen from:
      alkyl sulphates, alkyl ether sulphates, alkyl amidoether sulphates, alkylarylpolyether sulphates, monoglyceride sulphates, alkyl sulphonates, alkyl phosphates, alkylamide sulphonates, alkylaryl sulphonates, α-olefin sulphonates, paraffin sulphonates, alkyl sulphosuccinates, alkyl ether sulphosuccinates, alkylamide sulphosuccinates, alkyl sulphosuccinates; alkyl sulphoacetates; alkyl ether phosphates, acyl sarcosinates, acyl isethionates, N-acyl taurates, salts of any of the foregoing, fatty acid salts, coconut oil acid, hydrogenated coconut oil acid, acyl lactylates in which the acyl radical contains 8 to 20 carbon atoms, alkyl D-galactoside uronic acids and salts thereof, polyoxyalkylenated ($C_6$–$C_{24}$)alkyl ether carboxylic acids and salts thereof, polyoxyalkylenated ($C_6$–$C_{24}$)alkylaryl ether carboxylic acids and salts thereof, and polyoxyalkylenated ($C_6$–$C_{24}$) alkylamido ether carboxylic acids and salts thereof;
   (ii) Nonionic surfactants, said nonionic surfactants being chosen from:
      polyethoxylated, polypropoxylated or polyglycerolated fatty acids, alkylphenols, alpha-diols and alcohols, copolymers of ethylene oxide and of propylene oxide, condensates of ethylene oxide with fatty alcohols, condensates of propylene oxide with fatty alcohols, polyethoxylated fatty amides, polyglycerolated fatty amides containing on average from 1 to 5 glycerol groups, polyethoxylated fatty amines, oxyethylenated fatty acid esters of sorbitan having from 2 to 30 mol of ethylene oxide, fatty acid esters of sucrose, fatty acid esters of polyethylene glycol, alkylpolyglycosides, N-alkylglucamines, and amine oxides;

(iii) Amphoteric or zwitterionic surfactants, said amphoteric or zwitterionic surfactants being chosen from:
aliphatic secondary and tertiary amines in which the aliphatic radical is chosen from linear and branched chains containing 8 to 18 carbon atoms and containing at least one water-solubilizing anionic group, $(C_8-C_{20})$alkylbetaines, sulphobetaines, $(C_8-C_{20})$alkylamido$(C_1-C_6)$alkylbetaines, and $(C_8-C_{20})$alkylamido$(C_1-C_6)$alkylsulphobetaines; and
(iv) Cationic surfactants, said cationic surfactants being chosen from:
salts of optionally polyoxyalkylenated primary, secondary and tertiary fatty amines, quaternary ammonium salts, imidazolines, and cationic amine oxides;
b) at least one linear, saturated, long-chain fatty alcohol containing at least 70% by weight, relative to the total weight of said at least one linear, saturated, long-chain fatty alcohol, of at least one linear, saturated, long-chain fatty alcohol containing 22 carbon atoms; and
c) at least one additional ingredient chosen from opacifiers and pearlescent agents, said at least one additional ingredient being chosen from:
i) fatty dialkyl ethers which are solid at a temperature of less than or equal to 30° C., and
ii) alcohols containing from 27 to 48 carbon atoms and comprising one or two ether, one or two thioether, one ether and one thioether, one sulphoxide and one ether, or one or two sulphoxide groups, wherein said alcohols have a structure corresponding to formula (II):

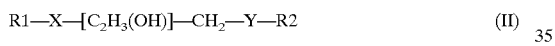

$$R1—X—[C_2H_3(OH)]—CH_2—Y—R2 \qquad (II)$$

in which R1 and R2, independently of each other, are chosen from linear $C_{12}$ to $C_{24}$ alkyl groups;
X is chosen from an oxygen atom, a sulphur atom, a sulphoxide group, and a methylene group;
Y is chosen from an oxygen atom, a sulphur atom, a sulphoxide group, and a methylene group;
wherein the sum of the number of carbon atoms present in the groups R1 and R2 has a value ranging from 24 to 44;
wherein when X denotes sulphoxide, Y does not denote sulphur, and
when Y denotes sulphoxide, X does not denote sulphur.

35. The cosmetic composition of claim 34, wherein
a) said at least one surfactant base is chosen from:
(i) said anionic surfactants,
wherein the alkyl or acyl radical of said anionic surfactants contains from 8 to 24 carbon atoms and the aryl radical is chosen from a phenyl group and a benzyl group,
wherein said salts of any of the foregoing anionic surfactants are chosen from alkali metal salts, ammonium salts, amine salts, amino alcohol salts, and magnesium salts,
wherein said fatty acid salts are chosen from oleic acid salts, ricinoleic acid salts, palmitic acid salts, and stearic acid salts,
wherein said polyoxyalkenated alkyl radicals contain from 2 to 50 ethylene oxide groups,
(ii) said nonionic surfactants,
wherein said polyethoxylated, polypropoxylated or polyglycerolated fatty acids, alkylphenols, alpha-diols and alcohols have a fatty chain containing 8 to 18 carbon atoms, and the number of ethylene oxide or propylene oxide groups range from 2 to 50 and the number of glycerol groups ranges from 2 to 30,
wherein said polyethoxylated fatty amides contain from 2 to 30 mol of ethylene oxide,
wherein said polyglycerolated fatty amides contain on average from 1.5 to 4 glycerol groups,
wherein said polyethoxylated fatty amines contain from 2 to 30 mol of ethylene oxide,
wherein said amine oxides are chosen from $(C_{10}-C_{14})$ alkylamine oxides and N-acylaminopropylmorpholine oxides;
(iii) said amphoteric or zwitterionic surfactants,
wherein within said amines, said at least one water-solubilizing group is chosen from carboxylate, sulphonate, sulphate, phosphate, and phosphonate,
wherein said amines are chosen from Amphocarboxyglycinates, with the structure

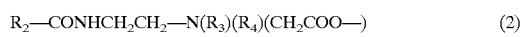

$$R_2—CONHCH_2CH_2—N(R_3)(R_4)(CH_2COO—) \qquad (2)$$

in which:
$R_2$ is chosen from an alkyl radical derived from an acid $R_2$—COOH present in hydrolyzed coconut oil, a heptyl radical, a nonyl radical, and an undecyl radical,
$R_3$ denotes a beta-hydroxyethyl group, and
$R_4$ denotes a carboxymethyl group; and
Amphocarboxypropionates, with the structure:

$$R_2—CONHCH_2CH_2—N(B)(C) \qquad (3)$$

in which:
B represents —$CH_2CH_2OX'$,
C represents —$(CH_2)_z$—Y', with z=1 or 2,
X' is chosen from a —$CH_2CH_2$—COOH group and a hydrogen atom,
Y' is chosen from a —COOH radical and a —$CH_2$—CHOH—$SO_3H$ radical,
$R_{2'}$ is chosen from an alkyl radical of an acid $R_9$—COOH present in an oil chosen from coconut oil and hydrolysed linseed oil, an alkyl radical, a $C_{17}$ alkyl radical and its iso form, and an unsaturated $C_{17}$ radical;
(iv) said cationic surfactants,
wherein said quaternary ammonium salts are chosen from the chloride and bromide salts of tetraalkylammonium, alkylamidoalkyltrialkylammonium, trialkylbenzylammonium, trialkylhydroxyalkylammonium and alkylpyridinium radicals;
c) said at least one additional ingredient, chosen from
i) said fatty dialkyl ethers which are dialkyl ethers of formula (I):

$$R—O—R' \qquad (I)$$

in which:
R and R', which are identical or different, are chosen from saturated and unsaturated, linear and branched alkyl radicals containing from 12 to 30 carbon atoms, R and R' being chosen such that the compound of formula (I) is solid at a temperature of less than or equal to 30° C.; and
ii) said alcohols of formula (II), wherein the sum of the number of carbon atoms present in the groups R1 and R2 has a value ranging from 28 to 40.

36. The composition according to claim 34, wherein
a) said at least one surfactant base is chosen from:
   i) alkyl sulphate and alkyl ether sulphate salts, and
   ii) alkylpolyglycosides.

37. The composition according to claim 35, wherein
a) said at least one surfactant base is chosen from:
   i) said anionic surfactants:
      wherein said alkali metal salts thereof are sodium salts;
   iii) said amphocarboxypropionates, in which $R_{2'}$ is chosen from a $C_7$ alkyl radical, a $C_9$ alkyl radical, a $C_{11}$ alkyl radical, and a $C_{13}$ alkyl radical;
c) said at least one additional ingredient is chosen from said dialkyl ethers of formula (I) wherein R and R' contain from 14 to 24 carbon atoms, and are identical, and from said alcohols of formula (II) wherein X denotes oxygen, Y denotes methylene, and R1 and R2 are chosen from radicals containing from 12 to 22 carbon atoms.

38. A method for suspending an insoluble conditioner in a cosmetic composition, comprising
mixing said insoluble conditioner with a solubilizing composition comprising:
   a) at least one surfactant base,
   b) at least one linear, saturated, long-chain fatty alcohol containing at least 50% by weight, relative to the total weight of said at least one linear, saturated, long-chain fatty alcohol, of at least one linear, saturated, long-chain fatty alcohol containing 22 carbon atoms, and
   c) at least one additional ingredient chosen from opacifiers and pearlescent agents, wherein said at least one additional ingredient is chosen from:
      i) fatty dialkyl ethers which are solid at a temperature of less than or equal to 30° C.,
      ii) alcohols containing from 27 to 48 carbon atoms and comprising one or two ether, one or two thioether, one ether and one thioether, one sulphoxide and one ether, or one or two sulphoxide groups, wherein said alcohols have a structure corresponding to formula (II):

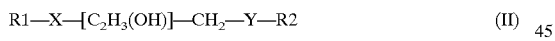

R1—X—[C$_2$H$_3$(OH)]—CH$_2$—Y—R2   (II)

in which R1 and R2, independently of each other, are chosen from linear $C_{12}$ to $C_{24}$ alkyl groups;
      X is chosen from an oxygen atom, a sulphur atom, a sulphoxide group, and a methylene group;
      Y is chosen from an oxygen atom, a sulphur atom, a sulphoxide group, and a methylene group;
      wherein the sum of the number of carbon atoms present in the groups R1 and R2 has a value ranging from 24 to 44;
      wherein when X denotes sulphoxide, Y does not denote sulphur, and
      when Y denotes sulphoxide, X does not denote sulphur; and
   mixing said solubilizing composition with said cosmetic composition.

39. The method according to claim 38, wherein said cosmetic composition is chosen from foaming, conditioning, and washing compositions.

40. A method for adding or improving a pearling effect in a cosmetic composition, comprising
mixing said cosmetic composition with a pearling base comprising:
   a) at least one surfactant base,
   b) at least one linear, saturated, long-chain fatty alcohol containing at least 50% by weight, relative to the total weight of said at least one linear, saturated, long-chain fatty alcohol, of at least one linear, saturated, long-chain fatty alcohol containing 22 carbon atoms, and
   c) at least one additional ingredient chosen from opacifiers and pearlescent agents, wherein said at least one additional ingredient is chosen from:
      i) fatty dialkyl ethers which are solid at a temperature of less than or equal to 30° C.,
      ii) alcohols containing from 27 to 48 carbon atoms and comprising one or two ether, one or two thioether, one ether and one thioether, one sulphoxide and one ether, or one or two sulphoxide groups, wherein said alcohols have a structure corresponding to formula (II):

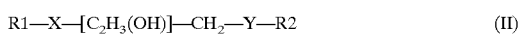

R1—X—[C$_2$H$_3$(OH)]—CH$_2$—Y—R2   (II)

in which R1 and R2, independently of each other, are chosen from linear $C_{12}$ to $C_{24}$ alkyl groups;
      X is chosen from an oxygen atom, a sulphur atom, a sulphoxide group, and a methylene group;
      Y is chosen from an oxygen atom, a sulphur atom, a sulphoxide group, and a methylene group;
      wherein the sum of the number of carbon atoms present in the groups R1 and R2 has a value ranging from 24 to 44;
      wherein when X denotes sulphoxide, Y does not denote sulphur, and
      when Y denotes sulphoxide, X does not denote sulphur.

41. The composition according to claim 1, wherein said composition is a pearling base.

42. A process for the cosmetic treatment of a keratin substance, comprising:
applying to said keratin substance a cosmetic composition which comprises:
   a) at least one surfactant base,
   b) at least one linear, saturated, long-chain fatty alcohol containing at least 50% by weight, relative to the total weight of said at least one linear, saturated, long-chain fatty alcohol, of at least one linear, saturated, long-chain fatty alcohol containing 22 carbon atoms, and
   c) at least one additional ingredient chosen from opacifiers and pearlescent agents, wherein said at least one additional ingredient is chosen from:
      i) fatty dialkyl ethers which are solid at a temperature of less than or equal to 30° C.,
      ii) alcohols containing from 27 to 48 carbon atoms and comprising one or two ether, one or two thioether, one ether and one thioether, one sulphoxide and one ether, or one or two sulphoxide groups, wherein said alcohols have a structure corresponding to formula (II):

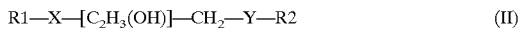

R1—X—[C$_2$H$_3$(OH)]—CH$_2$—Y—R2   (II)

in which R1 and R2, independently of each other, are chosen from linear $C_{12}$ to $C_{24}$ alkyl groups;
      X is chosen from an oxygen atom, a sulphur atom, a sulphoxide group, and a methylene group;

Y is chosen from an oxygen atom, a sulphur atom, a sulphoxide group, and a methylene group;

wherein the sum of the number of carbon atoms present in the groups R1 and R2 has a value ranging from 24 to 44;

wherein when X denotes sulphoxide, Y does not denote sulphur, and when Y denotes sulphoxide, X does not denote sulphur.

43. The process according to claim 42, wherein said keratin substance is a human keratin substance.

44. The process according to claim 43, wherein said human keratin substance is hair.

45. The process according to claim 42, further comprising the step of:

rinsing said keratin substance with water after said applying of said cosmetic composition.

\* \* \* \* \*

UNITED STATES PATENT AND TRADEMARK OFFICE
CERTIFICATE OF CORRECTION

PATENT NO.    : 6,521,238 B1
DATED         : February 18, 2003
INVENTOR(S)   : Muller et al.

It is certified that error appears in the above-identified patent and that said Letters Patent is hereby corrected as shown below:

Column 12,
Line 39, "sulphosuccinates;" should read -- sulphosuccinamates; --.

Column 14,
Line 31, "$R_2$-CONHCH$_2$CH$_2$-N(B)(C)" should read -- $R_{2'}$-CONHCH$_2$CH$_2$-N(B)(C) --.

Signed and Sealed this

Twenty-second Day of April, 2003

JAMES E. ROGAN
*Director of the United States Patent and Trademark Office*